United States Patent [19]
Foller et al.

[11] Patent Number: 5,250,162
[45] Date of Patent: Oct. 5, 1993

[54] METHOD OF REDUCING TI(IV) TO TI(III) IN ACID SOLUTION

[75] Inventors: Peter C. Foller, Boston; Ravi Vora, Framingham; Robert J. Allen, Saugus, all of Mass.

[73] Assignee: Metallgesellschaft AG, Frankfurt am Main, Fed. Rep. of Germany

[21] Appl. No.: 827,731

[22] Filed: Jan. 29, 1992

[51] Int. Cl.⁵ .............................................. C25C 1/06
[52] U.S. Cl. ............................................... 204/140
[58] Field of Search ......................................... 204/140

[56] References Cited
FOREIGN PATENT DOCUMENTS
1132996 10/1982 Canada .

Primary Examiner—T. Tufariello
Attorney, Agent, or Firm—Herbert Dubno

[57] ABSTRACT

A method of reducing Ti(IV) to Ti(III) in which the Ti(IV) in acid solution is fed to an electrochemical cell having a semi-hydrophobic gas diffusion anode to which hydrogen gas is supplied. A current is passed through the cell to effect the electrochemical reduction and the Ti(III) is recovered for use as a re-attack solution in titanium dioxide pigment production or for use in indirect organic reductions. Ti(III) salts may also be recovered for use, for example, in the reduction of organic compounds.

19 Claims, 4 Drawing Sheets

DIAGRAM OF CELL AND APPARATUS USED

DIAGRAM OF CELL IN FLOW-THROUGH CONFIGURATION

DIAGRAM OF CELL IN FLOW-PAST CONFIGURATION

METHOD OF REDUCING Ti(IV) TO Ti(III) IN ACID SOLUTION

FIELD OF THE INVENTION

Our present invention relates to a method for electrochemically reducing Ti(IV) to Ti(III) in acidic solutions serving as the electrolyte for the electrochemical process. More particularly, the invention is related to a method of producing Ti(III) solutions free of extraneous ions which can be used as reducing agents for organic compounds, which can enable Ti(III) salts to be produced in an efficient and economical manner or which can be used to transform Ti(IV) spent solutions into compositions which are more valuable.

BACKGROUND OF THE INVENTION

Ti(III) is a mild reducing agent of industrial importance. It has applications in the synthesis of organic compounds where a controlled and selective reduction of functional groups is desired.

Ti(III) sulfate in sulfuric acid is required as a so-called "re-attack" solution in the Sulfate Process for the production of pigment grade $TiO_2$. A stream of Ti(III) must be introduced in order to assure that the iron present in the ilmenite ($FeO \cdot TiO_2$) ore being leached by sulfuric acid is kept in the ferrous form. In the ferrous state, the iron remains soluble through the purification of the titanium dioxide product. Thus, ferrous ion is washed away, and a white pigment free of any iron coloration results.

Common methods for the reduction of Ti(IV) to Ti(III) include the use of either metallic aluminum or metallic zinc. In sulfuric acid, such methods require organic inhibitors, to reduce the parasitic evolution of hydrogen. Difficulties with such approaches are obvious, especially from an environmental aspect.

Currently, the Sulfate Process has about a 15% market share of the titanium dioxide pigment production business. Hence a new, environmentally more benign process for Ti(III) reagent preparation produces retrofit opportunities throughout the industry.

Ti(III) salts also constitute effective reducing agents for organic compounds.

OBJECTS OF THE INVENTION

It is, therefore, the principal object of the present invention to provide an improved method of reducing Ti(IV) to Ti(III), whereby drawbacks of the earlier technique can be avoided and, in particular, the reduction can be effected economically and in an environmentally sound manner.

It is also an object of the present invention to provide an improved method of producing crystalline Ti(III) salts and, more generally, to provide Ti(III) reagents useful in organic synthesis.

SUMMARY OF THE INVENTION

These objects and others which will become more readily apparent hereinafter are attained, in accordance with the present invention, in a method comprising the steps of:

(a) providing an electrochemical cell having a semi-hydrophobic gas diffusion anode and a cathode traversable by a liquid and coupled to the anode by a diffusion zone;

(b) feeding hydrogen gas to the anode;

(c) feeding an acidic solution of Ti(IV) to the cathode; and (d) impressing an electric current across the anode and the cathode to effect cathodic reduction of Ti(IV) similarly with anodic oxidation of hydrogen, thereby forming Ti(III) in solution.

The electrochemical cell may be either a divided or an undivided cell. In the case of a divided cell, separate cathode and anode compartments are provided and are separated by a semipermeable membrane. Two flow paths are required. Advantageously in the case of an undivided cell, the fuel cell type anode is laminated with a polymeric coating which both serves as a gas antipercolation layer, preventing escape of hydrogen into the electrolyte, preventing flooding of the anode, and also as a diffusion barrier to slow the transport of Ti(III) formed at the cathode. Without such a barrier, oxidation back to Ti(IV) may occur to a greater extent. In all cases described below, the fuel-cell-type anode is provided with platinum/ruthenium unless stated otherwise.

It has been found to be advantageous to operate the cell at a temperature in excess of 35° C. to achieve high current efficiencies, but at a temperature below 70° C. to avoid hydrolysis of Ti(IV) to titanium dioxide. The preferred temperature is 45° to 55° C.

While we have found that a variety of cathodic materials can be used, the best results appear to have been achieved with corrosion resistant steels or metal alloys such as Carpenter 20 alloy, corrosion resistant alloys like Hastalloy and Inconel, although lead, graphite and carbon may also be used. The corrosion resistant steel may be a stainless steel and preferably the cathode structure is in the form of an open work, for example, a mesh or expanded metal and, most desirably, as the description below will demonstrate, a plurality of layers of expanded metal or mesh.

We have found that the number of such layers should preferably range between two and eight with a number between four and six being most preferable.

The cathode may be a flow-through cathode in which the cathodic material is traversed by the electrolyte, or a flow-past cathode whereby the acidic electrolyte containing the Ti(IV) is fed in a plurality of passes across the cathode material in the cathode chamber.

The preferred solutions are solutions of the Ti(IV) sulfate, fluoborate, methanesulfonate and perchlorate, respectively in sulfuric acid, fluoboric acid, methane sulfonic acid and perchloric acid. Where a Ti(IV) sulfate in sulfuric acid is used, the preferred concentration of Ti(IV) sulfate is 5 to 20 weight percent and the preferred sulfuric acid concentration is 10-50 weight percent. Still more preferred are a Ti(IV) sulfate concentration of 5-10 percent by weight and a sulfuric acid concentration of 20-25 percent by weight.

According to the invention, the Ti(III) solution which is recovered from the cell can be used for reduction of an organic compound and the resulting Ti(IV) solution then recycled, if desired, to the electrochemical cell. Alternatively, the Ti(III) which is produced by the reduction may be crystallized from the electrolyte in the form of Ti(III) salts and then subjected to further purification if desired, or dissolved in an appropriate solvent to form a more concentrated or dilute Ti(III) reagent.

The Ti(III) reagents which are produced in accordance with the invention can be utilized for reduction of the nitro group of an organic compound to an amine.

The product thus is useful for the production of p-aminophenol. According to the invention, the electrochemical cell can be coupled continuously with the organic reactor so that the Ti(III) solution leaving the cell is delivered directly to the reactor in which the organic compound is reduced. The Ti(IV) solution leaving the reactor can be returned to the electrochemical cell in a continuous recirculation process.

The electrochemical reaction which is exploited by the invention is the sum of the half reactions.

At the anode:

$$H_2 = 2H^+ + 2e^-,$$

$$E^\cdot = 0.0 \text{ V}$$

At the cathode:

$$e^- + 2H^+ + TiO^{2+} = Ti^{3+} + H_2O,$$

$$E^\cdot = +0.10 \text{ V}$$

Overall electrochemical reaction:

$$2H^+ + H_2 + 2TiO^{2+} = 2Ti^{3+} + 2H_2O$$

Note that acid is consumed in the overall process. Water formed also dilutes the reagent to a minor extent.

The reaction is thermodynamically spontaneous. However, in practice, it does not occur by passing hydrogen through solutions of Ti(IV) salts. It is necessary to employ a catalyst for the dissociation of molecular hydrogen which is simultaneously in contact with the solution a source of hydrogen, and a conductive substrate upon which the reduction may take place. Even then, the reaction does not occur at acceptable rates at temperatures limited by the tendency for Ti(IV) to hydrolyze to $TiO_2$. Thus, in this invention, a specifically designed electrochemical cell enables the process to occur at controlled and acceptable rates and at a high faradaic efficiency by the application of impressed current.

The electrochemical cell uses a hydrogen depolarized anode as opposed to an oxygen evolving anode. Were oxygen evolution at an inert anode to be used as the anodic process, a membrane or separator would have to be used to keep Ti(III) from oxidizing at such a high potential anode and to separate the oxygen evolved from any hydrogen arising due to the parasitic reaction at the cathode. Such undivided cells would inherently present an explosion hazard. It is uncertain that any anode material except platinum would be suitable for oxygen evolution in the high concentrations of sulfuric acid at an elevated temperature used in Sulfate Process titanium dioxide plants. A membrane would have to be used and would add to both cell hardware costs and to the power consumption of the process.

BRIEF DESCRIPTION OF THE DRAWING

The above objects, features and advantages of our invention will become more readily apparent from the following description, reference being made to the accompanying drawing in which.

SPECIFIC DESCRIPTION

Figure 1:
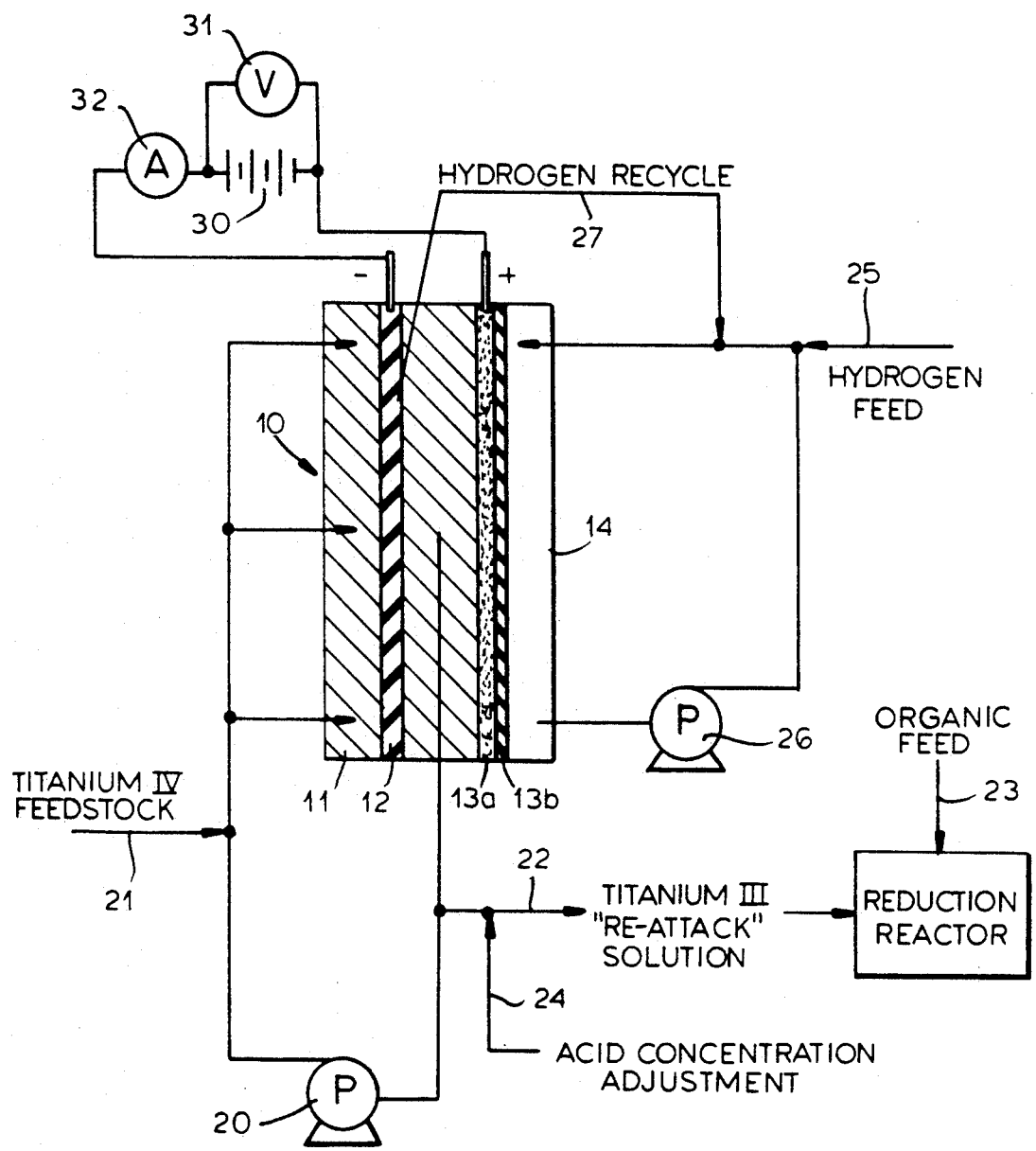
FIG. 1 is a diagram of an apparatus for carrying out the method of the invention, utilizing a flow through cathode.

The system shown in FIG. 1 comprises an electrochemical cell 10 of the full cell type utilizing a cathode compartment 11 with a flow-through cathode configuration which can consist of cathode material 12 in the form of a multiplicity of layers of Carpenter 20 alloy mesh, for example, opposite the coated anode 13a connected to the current collector 13b positioned adjacent to the anode gas compartment 14. A pump 20 recirculates the titanium salt solution which is acidic through the cell and the feed stock is supplied at 21 while the Ti(III) solution, which can be used as a reattack reagent in titanium dioxide pigment production is recovered at 22. If desired, the solution can be passed directly to a reactor 23 which is supplied with an organic feed for reduction. Acid concentration adjustment can be effected as represented by the feed line 24. Details of the cell construction are found in FIG. 3.

The hydrogen which forms the depolarizer at the anode is supplied by the hydrogen feed line 25 and can be recirculated by the pump 26. Any hydrogen which is generated by the parasitic cathode reaction is recycled as represented by the line 27. The current is passed through the cell from a current source represented at 30 and equipped with a voltmeter 31 and an ammeter 32.

Figure 3:
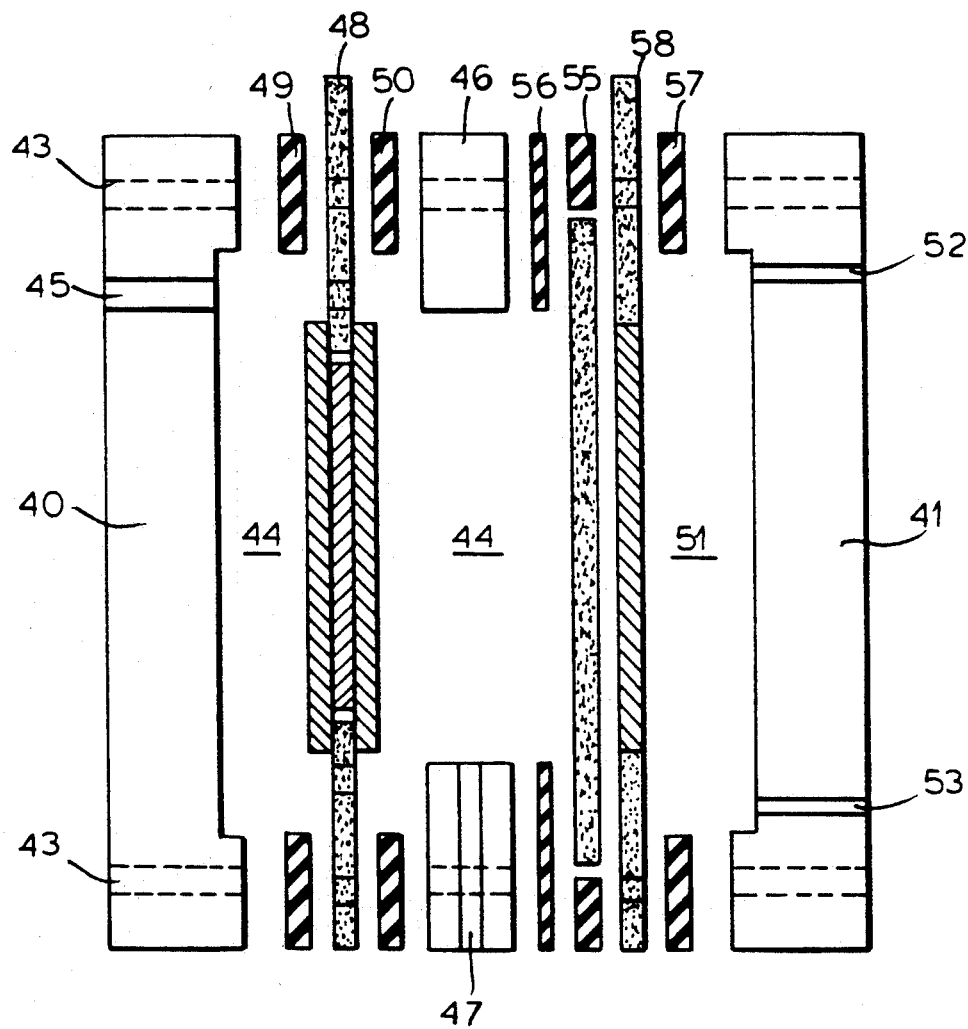
FIG. 3 is an exploded cross-sectional view of a flow-through-cell configuration according to the invention.

In FIG. 3, we have shown in somewhat greater detail the flow-through configuration of the cell which can be used.

In this configuration, the cell comprises a pair of end plates 40 and 41 which can be held together by bolts passing through the bores 43 to clamp the assembly together.

The electrolyte compartment is represented at 44 and receives the electrolyte from an inlet 45. The electrolyte outlet is formed in the spacer plate 46 at 47. Thus the electrolyte passes through the cathode assembly which comprises a mesh laminated cathode 48 flanked by electrically nonconducting gaskets 49 and 50.

The anode gas compartment is represented at 51 and hydrogen gas is fed thereto by an inlet 52, a gas outlet 53 likewise being provided in the end plate 41. The anode assembly 54 comprises an anode coated with platinum catalyst and overcoated with a polymeric membrane attached to a metal mesh current collector spot welded to a frame 55. Gasketing at 56 and 57 flanks the anode assembly and a current collector portion 58 allows connection of the positive terminal of the power source to the anode.

Figure 4:
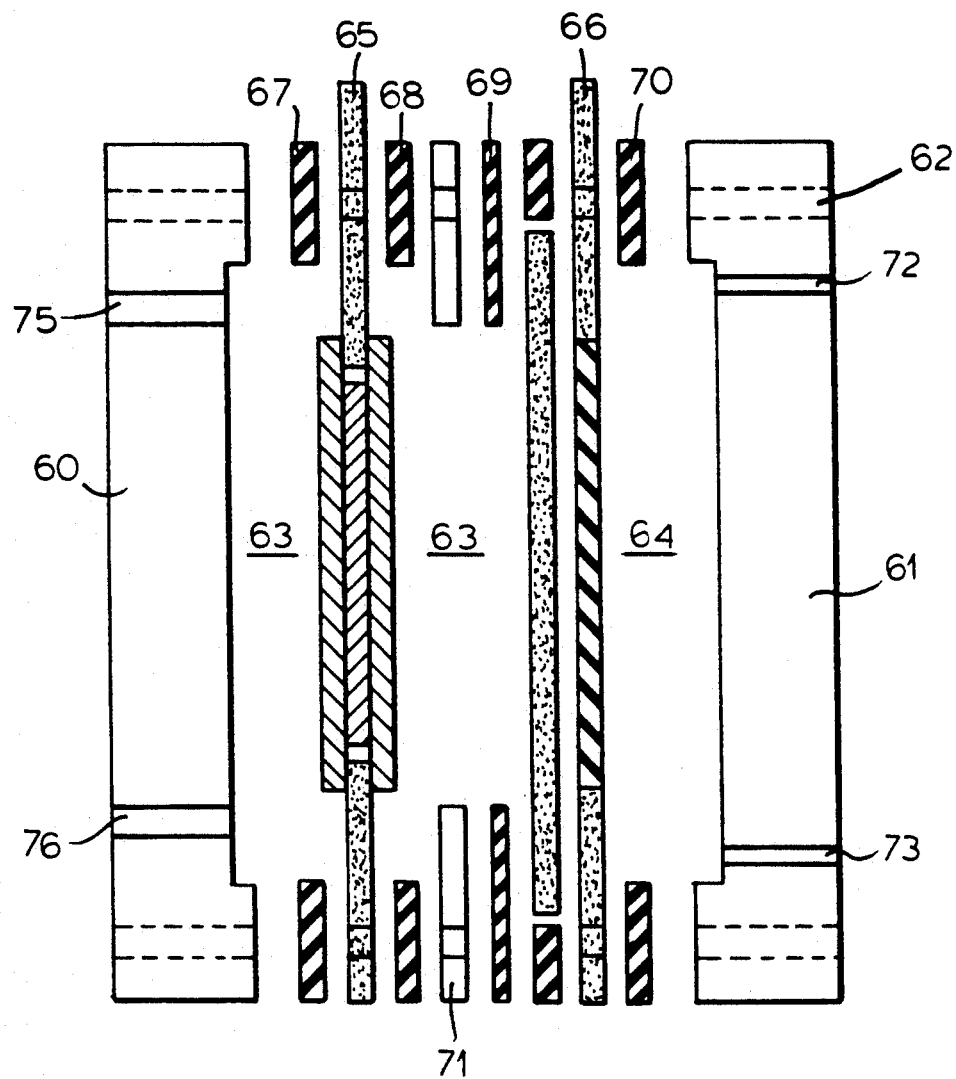
FIG. 4 is a similar view of a flow-past cell configuration.

The flow-past electrode assembly has been shown in FIG. 4 and is generally similar to that of FIG. 3. Here, however, the end plates 60 and 61 with the bores 62 for the clamping bolts, form the cathode compartment 63 and the anode compartment 64, respectively, with cathode 65 and anode 66 flanked by gaskets 67, 68, 69 and 70. The spacer 71 is smaller in this embodiment than in the embodiment of FIG. 3, since it need not have an outlet for the electrolyte. In this embodiment, the gas inlet and outlet are shown at 72 and 73, respectively, while the electrolyte inlet is formed at 74 in the end plate 60 which also has an electrolyte outlet 75.

SPECIFIC EXAMPLES

Cells of 100 cm$^2$ active electrode area were used. Two electrolyte flow configurations were evaluated. The cells have an internal volume of 100 ml in flow-past cathode configuration and 200 ml for flow-through cathode configuration (see FIG. 1). Electrolyte was circulated through the cells from a heated 2 liter reservoir via a peristaltic pump. The pump was capable of up to 150 ml/min flow rates. The cells included provisions for reference electrodes to monitor the individual potentials of the anode and the cathode.

The concentration of Ti(III) after electrochemical reduction was determined by means of a titration with ferric sulfate using potassium thiocyanate as the indicator. The red complex formed by the reaction of excess Fe(III) with thiocyanate marks the endpoint of the titration.

Titration Reaction:

$$Fe^{3+} + Ti^{3+} + H_2O = TiO^{2+} + Fe^{2+} + 2H^+$$

At the End Point $$Fe^{3+}(excess) + SCN^- = Fe(SCN)^{2+}(red\ color)$$

All experiments were performed using Ti(IV) solutions in sulfuric acid. High concentrations of Ti(IV) are unstable with respect to hydrolysis to $TiO_2$. The hydrolysis most readily occurs at low concentrations of acid and at high temperature.

Tests of Anode Materials

The electrochemical cell uses a fuel cell type gas diffusion anode. These typically consist of a carbon cloth, carbon paper, or judiciously selected metallic screen or exmet substrate catalyzed with finely divided platinum or platinum and ruthenium on high surface area carbon. Such electrodes have been developed over many years for use in fuel cell technology. In the experimental work we have performed, the active layer of the hydrogen diffusion anodes is prepared from teflon and platinum or platinum and ruthenium catalyzed high surface area carbon. This layer is applied to the surface of carbon cloth substrate and sintered in place with a heat treatment.

It is preferable to have an anti-percolation coating on the anode. A polymeric anti-percolation coating laminated onto the catalyst layer of the electrode prevents loss of hydrogen into the electrolyte. The coating also ensures that the electrode does not "flood" by acting as a barrier to the intrusion of electrolyte. Such coatings are particularly important if the electrodes are to operate at electrolyte depths of more than 15 cm or so.

Such polymeric coatings also can act as a diffusion barrier for Ti(III) ions in addition to serving as an anti-percolation coating. Such a diffusion barrier serves to reduce the re-oxidation of Ti(III) ions at the anode and allows very high conversions to Ti(III) even in multiple-pass electrolyte flow configuration through the electrochemical cell.

The coated catalyzed carbon cloth can be bonded to a current distributor with a conductive epoxy. This makes it easier to mount the anode in commercial cell hardware. For instance, metallic mesh of fairly high open area can be used for this purpose. Hydrogen flow can either be provided through the cloth (as in U.S. Pat. No. 5,047,153), or provided from behind the cloth in the event that it is bonded to the screen with a light coat of conducting epoxy.

When reference is made to the 213 Carbon Cloth, we intend to identify the Avcarb fabric style number 213 marketed by the Textron Specialty Materials subsidiary of Textron, Inc. This product has a weave of eight harness satin, a warp/fill construction of 28/28 yarns/inch, a weight of 13 to 13.5 ounces/sq. yard, a thickness of 60 to 65 mils and a composition of carbonized spun yarns which can be two-ply yarns of a denier of 1600 (g/9000 m), an elongation of 4.9 and a break load of 1.8 pounds.

The ideal cathode material should be resistant to corrosion in high concentrations of acid. Its corrosion resistance should not be based on the formation of a surface oxide coating which is reducible in the presence of Ti(III) ions.

Hydrogen evolution is a parasitic reaction at the cathode. Therefore, it was expected that a cathode made from a material with a high overpotential for hydrogen evolution would give best results. Based on these criteria, the two materials studied initially were graphite and lead.

Graphite Sheet Electrode

The electrochemical cell was operated using a polymer coated anode and a graphite plate electrode. The current efficiencies were extremely low at the desired current densities at temperatures up to 60° C. It was not possible to go any higher in temperature due to the tendency of the electrolyte employed to hydrolyze.

The results for graphite plate cathodes are summarized in Table 1.

TABLE 1

| Graphite Flat Plate Cathode | | | |
| --- | --- | --- | --- |
| Electrolyte Composition: 10.2 wt. % $TiO_2$, 30 wt. % $H_2SO_4$ | | | |
| Flow Rate (ml/min) | Temperature °C. | Current Density (A/m$^2$) | Current Eff. (%) |
| 25 | 40 | 500 | 1.9 |
| 25 | 60 | 500 | 4.9 |
| 25 | 40 | 1000 | 2.4 |

Lead Flat Plate Cathode

A lead flat sheet cathode was tried in a manner identical to the graphite plate since lead also has a high hydrogen evolution overpotential. The performance of lead cathodes is given in Table 2.

It can be seen that although the current efficiencies are better than graphite, they are still low at the desired current density and up to 60° C.

TABLE 2

| Lead Sheet Cathode | | | |
| --- | --- | --- | --- |
| Electrolyte Composition: 10.2 wt. % $TiO_2$, 30 wt. % $H_2SO_4$ | | | |
| Flow Rate (ml/min) | Temperature °C. | Current Density (A/m$^2$) | Current Eff. (%) |
| 25 | 40 | 500 | 6.8 |
| 25 | 60 | 500 | 19.3 |
| 25 | 80 | 500 | 25.3 |

In general, current efficiencies were very low when flat plate cathodes were used.

Expanded Lead Cathodes

Figure 2:
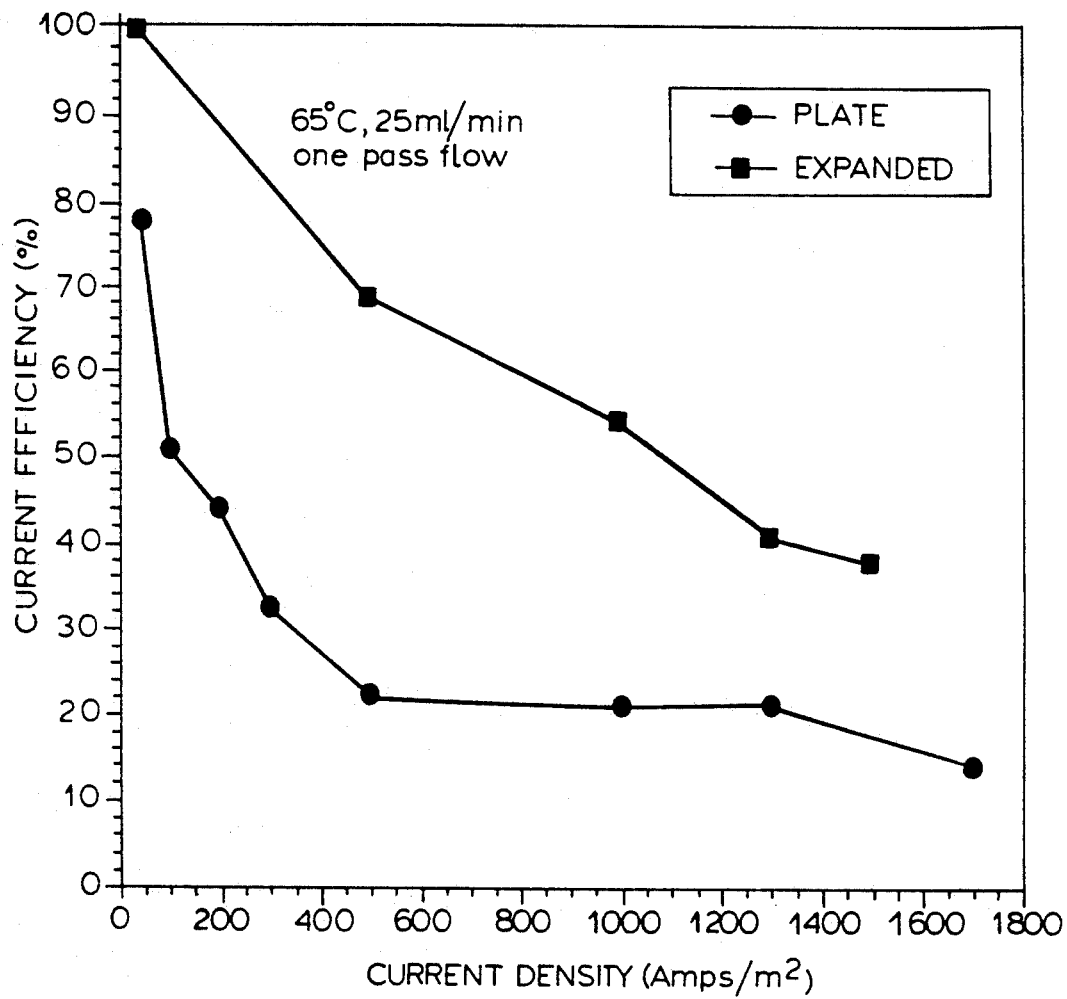
FIG. 2 is a graph illustrating features of the examples given below.

The lead plate cathode was substituted with one made from several laminations of expanded Pb metal. The current efficiencies obtainable became much larger when a lead mesh was substituted for lead sheet. FIG. 2 shows a comparison of lead plate cathodes to lead expanded metal cathodes; it shows a dramatic difference, confirming that low current densities on extended surface area materials are desirable.

Effect of Flow Rate

The effect of flow rate in a flow through configuration for a cell with a polymer coated anode and a lead exmet cathode is given in Table 3.

As seen in Table 3 higher flow rates are of benefit to current efficiency because mass transport of reactants and products is improved. Further, the acid consumed at the cathode is replenished such that hydrolysis is not forced by locally reduced hydrogen ion concentration in the diffusion layer adjacent to the electrode surface.

TABLE 3

Effect of Flow Rate on Current Efficiency

| | |
|---|---|
| Anode: | Polymer coated catalyzed 213 cloth |
| Cathode: | Pb expanded metal, 5 sheets |
| Electrolyte: | 1.1M Ti (IV), 3M $H_2SO_4$, single-pass, flow-through |
| Temperature: | 60° C. |
| Current Density: | 1,000 $A/m^2$ |

| Flow Rate (ml/min) | Current Efficiency (%) |
|---|---|
| 28.5 | 45.6 |
| 55.0 | 53.5 |
| 86.2 | 67.8 |
| 116.0 | 71.6 |

Effect of Temperature

Higher temperatures are beneficial to current efficiency. There is, however, a practical limitation in that unacceptable hydrolysis to titanium dioxide can occur at temperature above 65° C. See Table 4.

TABLE 4

Effect of Temperature

| | |
|---|---|
| Anode: | Polymer coated catalyzed 213 cloth |
| Cathode: | Lead exmet 5 sheets, not spot-welded |
| Electrolyte: | 1.1M Ti (IV), 3M $H_2SO_4$, single-pass, |
| Flow Rate: | 25 ml/min |
| Current Density: | 1,000 $A/m^2$ |

| Temperature (°C.) | Current Efficiency (%) |
|---|---|
| 40 | 16.8 |
| 45 | 19.9 |
| 50 | 21.7 |
| 55 | 35.5 |
| 60 | 42.1 |

Conversion Experiments with Lead Exmet Cathode

The following results are from a cell using a polymer coated anode and a 5 sheet lead exmet cathode at 60° C. at an electrolyte flow rate of 115 ml/min.

Table 5 gives the conversion vs. time for the lead exmet cathode. After operating for about 30 minutes the current efficiency drops for each time segment thereafter. The cell voltage increases with time. After four hours, the cathode has a jelly-like deposit on it which contributed to increased cell voltage and lowered current efficiency.

TABLE 5

Conversion Using a Lead Exmet Cathode

| | |
|---|---|
| Anode: | Polymer coated catalyzed 213 cloth |
| Cathode: | 5-sheet lead expanded metal cathode |
| Electrolyte: | 1.1M Ti (IV) 30 wt. % $H_2SO_4$. Total volume = 1 liter |
| Conditions: | 1,000 $A/m^2$, 60° C., 115 ml/min flow rate Flow-through cathode. Recycled flow. |

| Time (min) | Cell Voltage (V) | Time Segment C.E. (%) | Total Moles Converted (%) |
|---|---|---|---|
| 15 | 1.02 | 79 | 3.5 |
| 32 | 1.22 | 83 | 7.3 |
| 65 | 1.32 | 59 | 12.8 |
| 113 | 1.41 | 37 | 17.8 |
| 148 | 1.41 | 14 | 19.2 |
| 191 | 1.42 | 9 | 20.3 |
| 238 | 1.47 | 8 | 21.4 |

When lead exmet cathodes and the electrolyte described in Table 5 were used, the fraction of conversion appears to be limited to about 25% by the cathode fouling. The fouling reduces the effective surface area of the cathode. This increases the parasitic hydrogen evolution during the processing of a batch of Ti(IV), and the current efficiency of the cell is seen to decline rapidly with increasing amounts of Ti(IV) converted. The fouling is felt to be due to hydrolysis of Ti(IV) on the surface of the lead cathodes caused by locally depleted hydrogen ion. In practice, it is undesirable to have lead contamination in any process that makes pigments. Lead cathodes would need to be cathodically protected at all time to prevent this.

The work with lead cathodes gave less than satisfactory results primarily due to hydrolysis at the cathode. Therefore, the following information was developed on the stability of Ti(IV) solutions in sulfuric acid.

Stability Studies for Ti(IV) Electrolytes

The following experimentation was performed to study the stability to hydrolysis of sulfuric acid solutions of Ti(IV) in support of the application of the invention to Sulfate Process titanium dioxide pigment production.

In the titanium dioxide pigment production industry, titanium concentration is expressed in terms of "$TiO_2$" content. This practice has been adopted.

Four solutions with different Ti(IV) and acid concentrations are shown in Table 6. These were prepared from a solution obtained from a sulfate process titanium dioxide plant of the following composition: 15.5 wt.% "$TiO_2$," 40 wt.% $H_2SO_4$.

TABLE 6

| | Composition of Solutions Studied | |
|---|---|---|
| Solution | "$TiO_2$" (wt. %) | $H_2SO_4$ (wt. %) |
| A | 7.2 | 45 |
| B | 9.8 | 25 |
| C | 12.0 | 31 |
| D | 10.5 | 39.5 |

Solution B was the most stable of the four solutions studied. While an insoluble precipitate formed in all other solutions, Solution B did not have any precipitate after 2 weeks at room temperature. Thus, this composition was selected for further experimental study. Though more dilute than the other compositions studied, this is an acceptable composition for Ti(III) solutions used in the Sulfate Process.

Carpenter 20 Cathodes

Carpenter 20 is a special corrosion resistant stainless steel designed specifically for acid service. It has the composition 35% Ni, 20% Cr, 40% Fe, 4% Cu, and 3% Mo. It is economical, has good mechanical properties and is easy to fabricate. There is no need for continuous cathodic protection with Carpenter 20 in sulfuric acid at room temperature.

The information from all previous results was combined to study the use of Carpenter 20 at current densities similar to those provided by 5 laminations of lead mesh. Tables 7 to 11 show the excellent results obtained.

Hydrogen evolution at the cathode is a parasitic reaction that leads to reduced current efficiencies. Therefore, it is desirable to suppress the evolution of hydrogen. In conventional situations, this is done by the selection of a cathode material with a high hydrogen evolution overpotential. Lead, for instance, has a high hydrogen overpotential in acid solutions. The reduction of Ti(IV), however, requires the simultaneous reaction of hydrogen ion. Materials which inhibit the discharge of hydrogen ion and the association of absorbed hydrogen atoms may also retard the reduction of Ti(IV) as well as the evolution of hydrogen. Thus materials like Carpenter 20, which have a lower hydrogen overvoltage than lead, function just as well as or better than lead after optimization of reaction conditions.

Results for Carpenter 20 cathodes

Using Solution B of Table 6 (9.8 wt.% "TiO$_2$" and 25 wt.% H$_2$SO$_4$), and a laminate made from 4 sheets of Carpenter 20 mesh as the cathode material, it has proved possible to obtain conversions of up to 80% of the Ti(IV) originally present in the electrolyte at lower cell voltages. However, the current efficiency drops to less than 50% at 80% conversion.

TABLE 7

4-Sheet Carpenter 20 Mesh Cathode

| Anode: | Polymer coated catalyzed 213 cloth |
| Cathode: | 4-Sheet Carpenter 20 mesh cathode |
| Electrolyte: | 9.8 wt. % TiO$_2$, 25 wt. % H$_2$SO$_4$. |
| | Total volume = 1 liter |
| Conditions: | 1,000 A/m$^2$, 45° C., 70 ml/min flow rate |
| | Flow-through cathode. Recycled flow. |

| Time (min) | Total Moles Converted (Moles) | Total Percent Converted (%) | Cell Voltage (V) | Time Segment Current Efficiency (%) |
|---|---|---|---|---|
| 60  | 0.33 | 20.7 | 0.605 | 91 |
| 120 | 0.63 | 38.0 | 0.678 | 78 |
| 180 | 0.92 | 56.3 | 0.847 | 80 |
| 240 | 1.17 | 70.9 | 1.208 | 64 |
| 300 | 1.34 | 81.4 | 1.161 | 47 |
| 348 | 1.37 | 83.5 | 1.187 | 9 |

The number of laminations was doubled to eight. The results are shown in Table 8. It can be seen that the results are not as good as when there were only four laminations. The current efficiency dropped to about 53% at only 46% conversion.

TABLE 8

8-Sheet Carpenter Mesh Cathode

| Anode: | Polymer coated catalyzed 213 cloth |
| Cathode: | 8-Sheet Carpenter 20 mesh cathode |
| Electrolyte: | 9.8 wt. % TiO$_2$, 25 wt. % H$_2$SO$_4$. |
| | Total volume = 1.75 ml |

TABLE 8-continued

| Conditions: | 1,000 A/m$^2$, 45° C., 70 ml/min flow rate |
| | Flow-through cathode. Recycled flow. |

| Time (min) | Total Moles Converted | Percent Moles Converted (%) | Cell Voltage (V) | Time Segment Current Efficiency (%) |
|---|---|---|---|---|
| 70  | 0.393 | 13.6 | 0.684 | 91 |
| 135 | 0.864 | 30   | 0.788 | 100 |
| 200 | 1.130 | 39   | 0.965 | 65 |
| 265 | 1.320 | 46   | 1.250 | 53 |

Modified Polymer Coated Catalyzed 213 Cloth Anode

The results were slightly improved when a modified polymer coated anode was substituted for the standard coating. However, the modified anodes have an economic advantage. They can be fabricated very easily as compared to standard coated anodes. They would, therefore, be preferred.

TABLE 9

Modified Polymer Anode and Carpenter Mesh Cathode at 45° C.

| Anode: | Polymer coated catalyzed 213 cloth |
| Cathode: | 4-Sheet Carpenter 20 mesh cathode |
| Electrolyte: | 9.8 wt. % TiO$_2$, 25 wt. % H$_2$SO$_4$. |
| | Total volume = 1.0 liters |
| Conditions: | 1,000 A/m$^2$, 45° C., 70 ml/min flow rate |
| | Flow-through cathode. Recycled flow. |

| Time (min) | Total Moles Converted | Percent Moles Converted (%) | Cell Voltage (V) | Time Segment Current Efficiency (%) |
|---|---|---|---|---|
| 65  | 0.386 | 23.0 | 0.408 | 95 |
| 125 | 0.756 | 45.6 | 0.617 | 99 |
| 165 | 0.952 | 57.6 | 0.882 | 100+ |
| 185 | 1.062 | 65.0 | 0.890 | 87 |
| 212 | 1.272 | 77.0 | 1.170 | 83 |
| 240 | 1.344 | 81.0 | 1.130 | 35 |

Determination of Optimum Operating Temperature

It was necessary to determine the best operating temperature for the cell where it would be possible to obtain even higher conversions without any hydrolysis of electrolyte. Increasing the temperature to 55° C. helped in achieving higher conversions. From Table 10, it can be seen that when a polymer coated anode was used at 55° C., the conversions were as high as 96%.

TABLE 10

Celgard Anode and Carpenter Mesh Cathode at 55° C.

| Anode: | Polymer coated catalyzed 213 cloth. |
| Cathode: | 4-Sheet Carpenter 20 mesh cathode. |
| Electrolyte: | 9.8 wt. % TiO$_2$, 25 wt. % H$_2$SO$_4$. |
| | Total Volume: 1 liter |
| Conditions: | 1,000 A/m$^2$, 55° C., 70 ml/min flow rate |
| | Flow-through cathode. Recycled flow. |

| Time (min) | Total Moles Converted | Percent Moles Converted (%) | Cell Voltage (V) | Time Segment Current Efficiency (%) |
|---|---|---|---|---|
| 30  | 0.148 | 9  | 0.355 | 80 |
| 65  | 0.331 | 20 | 0.455 | 83 |
| 125 | 0.768 | 46 | 0.627 | 94 |
| 155 | 0.988 | 60 | 0.828 | 100+ |
| 200 | 1.180 | 71 | 1.077 | 69 |
| 240 | 1.420 | 86 | 1.114 | 86 |
| 310 | 1.580 | 96 | 1.366 | 41 |

Uncoated Anodes

It is possible to get good electrochemical reuslts with uncoated anodes. However, operation of such a cell is difficult because of the tendency of hydrogen gas to percolate through the anode and cause flooding of the feed plenum. Table 11 shows the results of a conversion study done with an anode which was not coated with a polymeric coating.

TABLE 11

Uncoated Anode and Carpenter Mesh Cathode at 55° C.

| | |
|---|---|
| Anode: | Uncoated Anode. |
| Cathode: | 4-Sheet Carpenter 20 mesh cathode. |
| Electrolyte: | 9.8 wt. % $TiO_2$, 25 wt. % $H_2SO_4$. Total Volume: 0.8 liters |
| Conditions: | 1,000 $A/m^2$, 55° C., 70 ml/min flow rate Flow-through cathode. Recycled flow. |

| Time (min) | Total Moles Converted | Percent Moles Converted (%) | Cell Voltage (V) | Time Segment Current Efficiency (%) |
|---|---|---|---|---|
| 40 | 0.186 | 14 | 0.535 | 75 |
| 75 | 0.396 | 30 | 0.543 | 94 |
| 110 | 0.537 | 41 | 0.624 | 85 |
| 160 | 0.765 | 58 | 1.006 | 73 |
| 195 | 0.920 | 70 | 1.118 | 71 |

In the case of Ti(IV) sulfate in sulfuric acid, it is desirable to use concentrations of 9.8 wt.% "$TiO_2$" and 25 wt.% $H_2SO_4$. An electrolyte of this composition is stable to hydrolysis and has given high current efficiencies, and low cell voltages.

A cathode consisting of four laminations of Carpenter 20 number 10 woven mesh has given the best results so far, thus confirming the desirability of using high surface area cathodes. It is readily available material and is not expensive. It is known to be stable to sulfuric acid, and no corrosion or cathode fouling problems have emerged in the experimental testing.

High flow rates are beneficial to the mass transport of reactants to the cathodes surface, and of product away from it. Any hydrogen that is evolved can also be readily swept out away. The increased turbulence produced by higher flow rates increases current efficiency and apparently prevents fouling of the cathode with $TiO_2$ which can form through the hydrolysis of Ti(IV) in regions of locally depleted hydrogen ion. A flow-through cathode arrangement is desirable.

Initial current efficiencies of over 90% can be obtained at current densities of 1,000 $A/m^2$ in the case that the preferred conditions recommended herein are employed.

Current efficiencies are higher at higher temperature. Above 65° C. there is increased tendency for hydrolysis of Ti(IV) to $TiO_2$, so it is preferable to operate at lower temperatures. It has been found that 45° C. is as high as is required for acceptable current efficiencies at 1,000 $A/m^2$ in the case that Carpenter 20 mesh cathodes are used. At this temperature, no hydrolysis problems either within the cell or on the cathode, are apparent.

Conversions of 75% and greater are achievable with electrolyte recycle. Single pass conversion is difficult from an engineering standpoint due to the simultaneous requirement for a fast flow to obtain high current efficiencies and to prevent hydrolysis at the cathode. Thus, recirculating flow through the electrochemical reactor is the preferred mode of operation of the process.

It is possible to precipitate Ti(III) sulfate by going to high conversions (more than 70%). After cooling the Ti(III) salt precipitates out. It is similarly expected that Ti(III) salts can be precipitated from the other possible electrolytes.

It has been found that the electrochemical cell technology described above is suitable for the preparation of other metal ion reductants in acid electrolytes, namely Cr(II), V(II), and Sn(II). These reductants can also be conveniently cathodically prepared versus hydrogen diffusion anodes. The incentive for performing the reduction in this manner is that no foreign ions are introduced into the product, as is inherent with either aluminum or zinc metal reduction, the common alternatives.

We claim:

1. A method of reducing Ti(IV) to Ti(III), comprising the steps of:
    (a) providing an electrochemical cell having a semi-hydrophobic gas diffusion anode and a cathode traversable by a liquid and coupled to said anode by a diffusion zone;
    (b) feeding hydrogen gas to said anode;
    (c) feeding an acidic solution of Ti(IV) to said cathode, said acidic solution comprising an acid selected from the group which consists of sulfuric acid, fluoroboric acid, methane sulfonic acid and perchloric acid in a concentration sufficient to retain Ti(IV) in solution; and
    (d) impressing an electric current across said anode and said cathode to effect cathodic reduction of Ti(IV) similarly with anodic oxidation of hydrogen, thereby forming Ti(III) in solution.

2. The method defined in claim 1 wherein said anode is coated with a polymeric coating forming an antipercolation layer preventing escape of hydrogen into said solution, and limiting the penetration of electrolyte into the anode, forming a diffusion barrier slowing transport of cathodically formed Ti(III)

3. The method defined in claim 1 wherein said anode does not have a polymeric coating of any kind.

4. The method defined in claim 1, further comprising the step of maintaining a temperature in said cell between substantially 35° C. and 70° C.

5. The method defined in claim 3 wherein said temperature is maintained between 45° C. and 55° C.

6. The method defined in claim 1 wherein said cathode is composed of a cathode material selected from the group which consists of corrosion resistant steel, corrosion resistant nickel alloys, lead, graphite and carbon.

7. The method defined in claim 5 wherein said cathode material is a corrosion resistant stainless steel having the composition of substantially 35% nickel, 20% chromium, 4% copper, 3% molybdenum and balance iron.

8. The method defined in claim 1 wherein said cell is formed at least in part by a plurality of layers of open work metal.

9. The method defined in claim 7 wherein said open work metal is a mesh.

10. The method defined in claim 7 wherein said open work metal is an expanded metal.

11. The method defined in claim 7 wherein said cathode is formed for multi-pass flow of said solution in a rapid turbulent flow passed across the surface of or through said cathode material.

12. The method defined in claim 1 wherein said solution is a solution of Ti(IV) sulfate in sulfuric acid, Ti(IV) fluoborate in fluoboric acid, Ti(IV) methane sulfonate in methane sulfonic acid or Ti(IV) perchlorate in perchloric acid.

13. The method defined in claim 11 wherein said solution is a solution of Ti(IV) sulfate in sulfuric acid with a concentration of titanium sulfate between substantially 5 wt.% and 20 wt.% and a concentration of sulfuric acid between 10 wt.% and 50 wt.%.

14. The method defined in claim 12 wherein the concentration of titanium sulfate in said solution is 5 to 10 wt.% and the concentration of sulfuric acid in said solution is 20 to 25 wt.%.

15. The method defined in claim 1 wherein said solution is a solution of Ti(IV) in sulfuric acid, said method further comprising the step of recovering the Ti(III) in a sulfuric acid solution and controlling therewith a concentration of ferric ion in a sulfate process titanium dioxide pigment production plant.

16. The method defined in claim 1 further comprising recovering Ti(III) from said cell and feeding the Ti(III) thus produced to a reactor for reduction of an organic compound.

17. The method defined in claim 15, further comprising recycling Ti(IV) recovered from reduction of said organic compound to said cell.

18. The method defined in claim 1 further comprising the step of recovering a Ti(III) salt solution from said cell and crystallizing a Ti(III) salt therefrom.

19. The method defined in claim 1 wherein higher oxidation states of vanadium are reduced to vanadium (II), or higher oxidation states of chromium are reduced to chromium (II), or higher oxidation states of tin are reduced to tin (II).

* * * * *